United States Patent [19]
Bagby

[11] Patent Number: 5,885,287
[45] Date of Patent: *Mar. 23, 1999

[54] SELF-TAPPING INTERBODY BONE IMPLANT

[75] Inventor: George Bagby, Spokane, Wash.

[73] Assignee: Spine-Tech, Inc., Minneapolis, Minn.

[ * ] Notice: The term of this patent shall not extend beyond the expiration date of Pat. No. 5,709,683.

[21] Appl. No.: 939,290

[22] Filed: Sep. 29, 1997

Related U.S. Application Data

[63] Continuation of Ser. No. 577,143, Dec. 19, 1995, Pat. No. 5,709,683.

[51] Int. Cl.⁶ .................................................. A61B 17/70
[52] U.S. Cl. ................................ 606/61; 606/72; 623/17
[58] Field of Search ................................ 606/61, 62, 65, 606/66, 72, 73, 86; 623/16, 17; 411/411, 414, 424

[56] References Cited

U.S. PATENT DOCUMENTS

| | | | |
|---|---|---|---|
| 3,989,284 | 11/1976 | Blose | 285/332.2 |
| 4,662,891 | 5/1987 | Noiles | 623/22 |
| 4,778,469 | 10/1988 | Lin et al. | 623/16 |
| 4,828,563 | 5/1989 | Muller-Lierheim | 623/16 |
| 4,834,757 | 5/1989 | Brantigan | 623/17 |
| 4,878,915 | 11/1989 | Brantigan | 623/17 |
| 4,946,378 | 8/1990 | Hirayama et al. | 623/17 |
| 4,961,740 | 10/1990 | Ray et al. | 606/61 |
| 5,015,247 | 5/1991 | Michelson | 606/61 |
| 5,055,104 | 10/1991 | Ray | 606/61 |
| 5,074,880 | 12/1991 | Manset | 623/20 |
| 5,084,050 | 1/1992 | Draenert | 606/77 |
| 5,171,327 | 12/1992 | Koch et al. | 623/16 |
| 5,263,953 | 11/1993 | Bagby | 606/61 |
| 5,403,136 | 4/1995 | Mathys | 411/310 |
| 5,423,817 | 6/1995 | Lin | 606/61 |
| 5,443,515 | 8/1995 | Cohen et al. | 623/17 |
| 5,489,307 | 2/1996 | Kuslich et al. | 623/17 |
| 5,489,308 | 2/1996 | Kuslich et al. | 623/17 |
| 5,499,892 | 3/1996 | Reed | 411/5 |
| 5,534,031 | 7/1996 | Matsuzaki et al. | 623/17 |

FOREIGN PATENT DOCUMENTS

3505567 A1  6/1986  Germany.

OTHER PUBLICATIONS

*Stress Shielding Reduced by a Silicon Plate–Bone Interface*, Donna L. Korvick, Jarrett W. Newbrey, George W. Bagby, Ghery D. Pettit & James D. Lincoln, Acta Orthop Scand; 1989, 60(5):611–6, pp. 611–616.

*Transmission of Disease Through Transplantation of Musculoskeletal Allografts*, The Journal of Bone and Joint Surgery, Nov. 1995 77–A, pp. 1742–1754.

*Anterior Cervical Interbody Fusion with Threaded Cylindrical Bone*, Jose M. Otero Vich, M.D., J. Neurosurg, vol. 63, Nov., 1985, pp. 750–753.

*Primary Examiner*—Michael Buiz
*Assistant Examiner*—David O. Reip
*Attorney, Agent, or Firm*—Wells, St. John, Roberts, Gregory & Matkin, P.S.

[57] ABSTRACT

A bone joining implant has a rigid, implantable base body having an outer surface with at least one bone bed engaging portion configured for engaging between a pair of bone bodies to be joined. At least one spline is provided by the bone bed engaging portion, the spline being constructed and arranged to extend outwardly of the body and having an undercut portion. Upon implantation, the undercut portion of the implant is configured to engage with a bone bed provided in the bone bodies to be joined so as to provide instantaneous fixation there between. In one embodiment, the implant is a vertebral interbody fusing device. The base body is cylindrical and the spline is an undercut thread helically configured about the body. In another embodiment, the base body forms a bridging portion for encircling a vertebra to be removed, and splines in the form of strips of material extend outwardly of top-most and bottom-most portions of the body. Each spline has a undercut portion such that each spline mates in interlocking engagement with top-most and bottom-most neighboring vertebra having bone beds for receiving the splines there along. The mid-most vertebra is then removed (corpectomy), after which an enforcing brace is received therein.

23 Claims, 14 Drawing Sheets

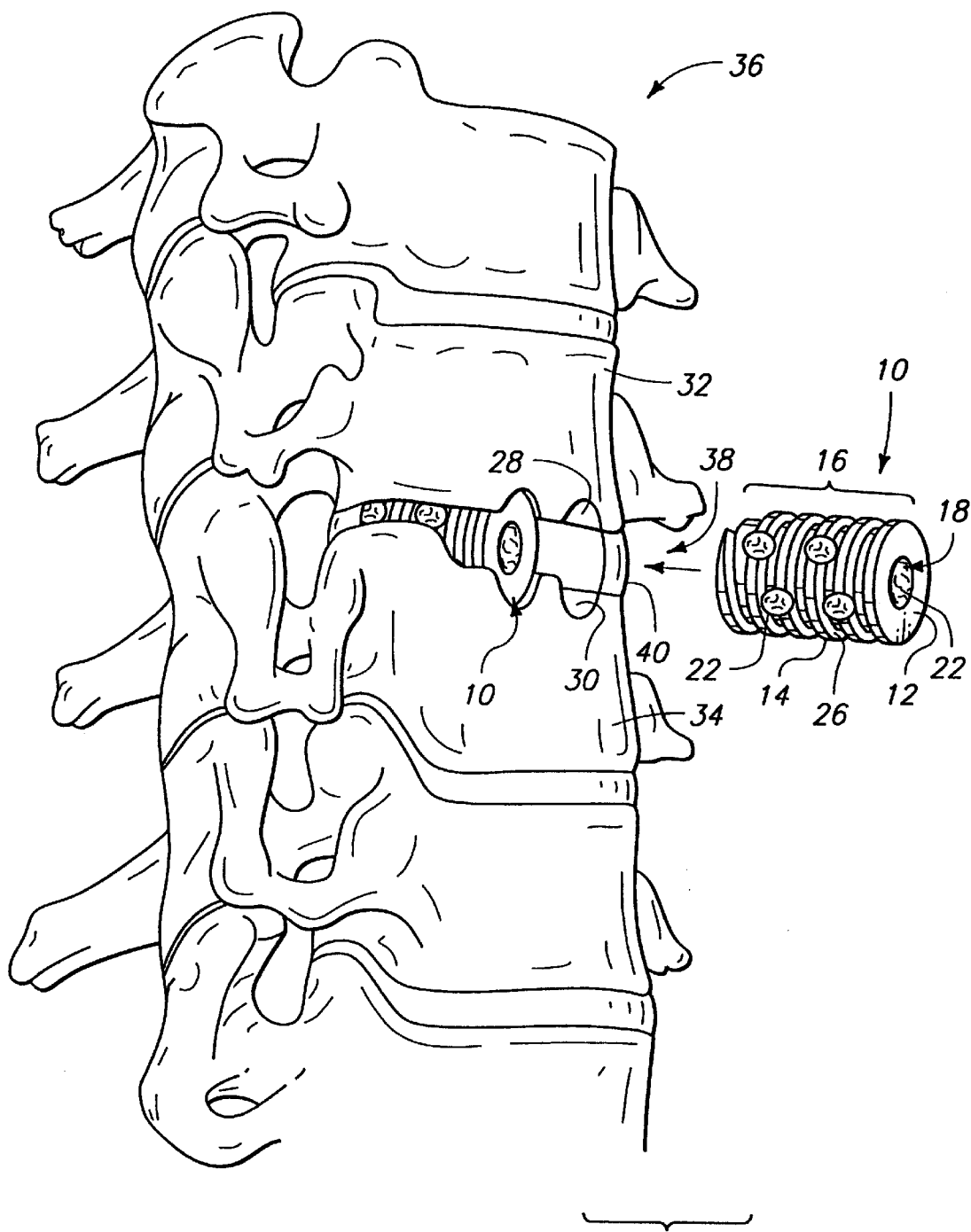

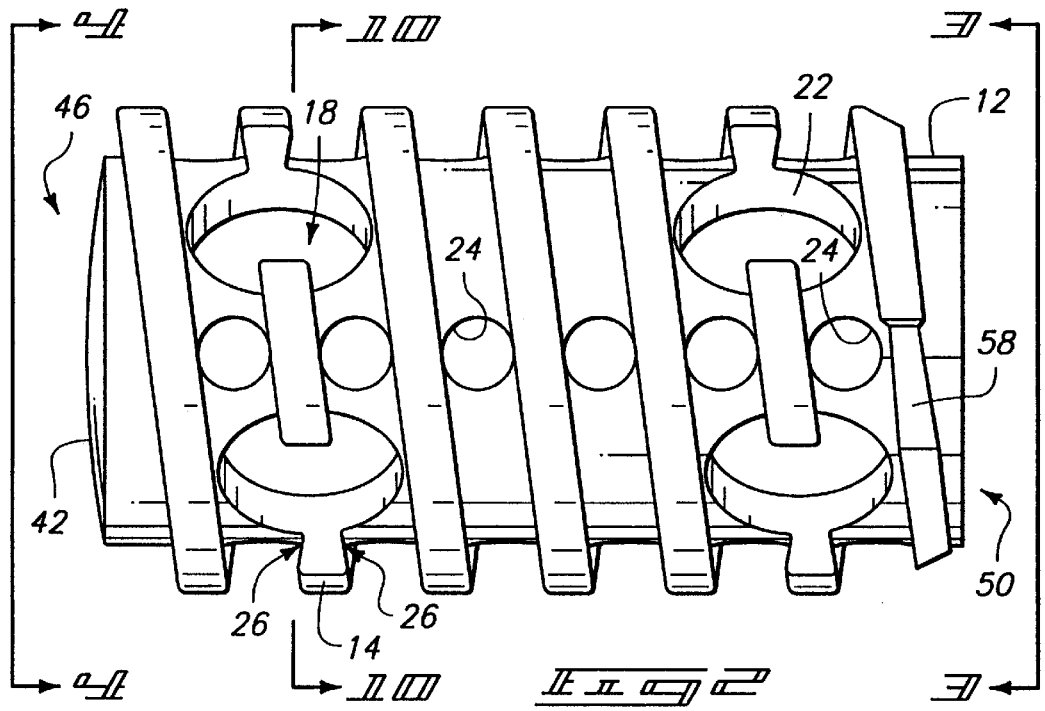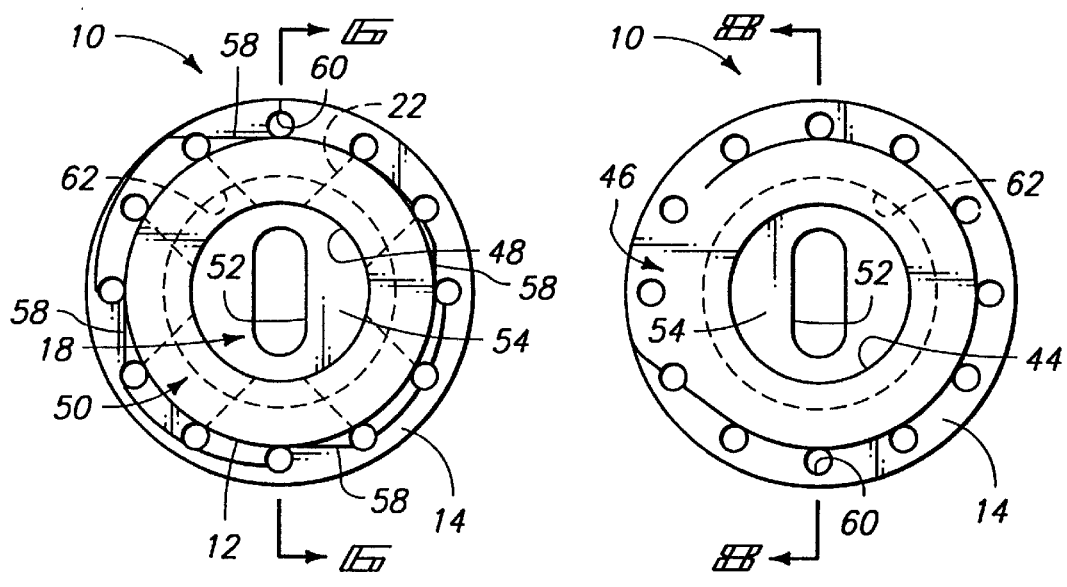

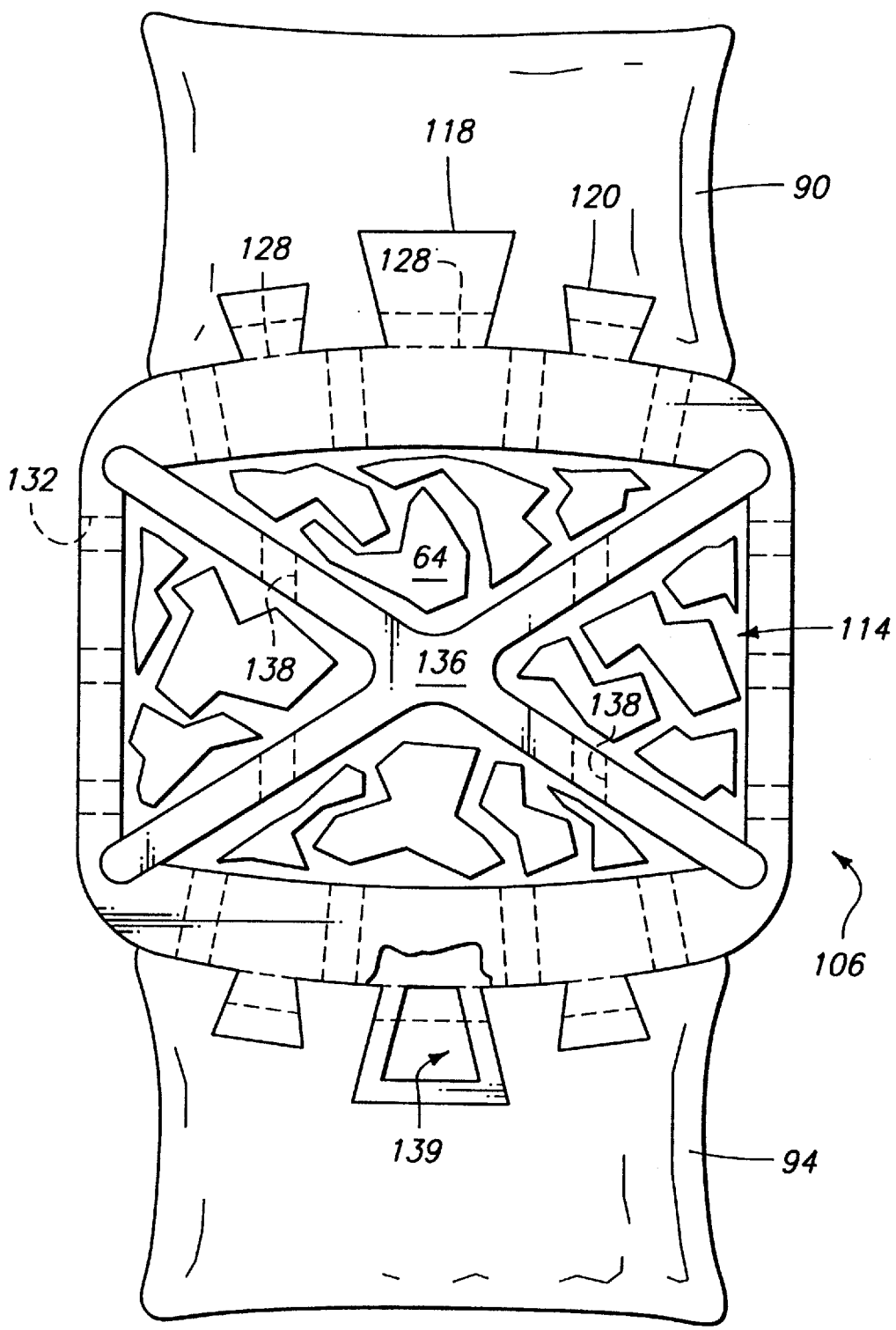

SELF-TAPPING INTERBODY BONE IMPLANT

RELATED PATENT DATA

This patent resulted from a continuation application of U.S. patent application Ser. No. 08/577,143, filed on Dec. 19, 1995 U.S. Pat. No. 5,709,683, entitled "Interbody Bone Implant Having Conjoining Stabilization Features for Bony Fusion".

TECHNICAL FIELD

This disclosure relates to surgical joining of bone bodies, and more particularly to instant fixation and staged bone fusion of bone bodies, such as spinal vertebrae.

BACKGROUND OF THE INVENTION

Although the immediate effort leading to this disclosure is directed to ward the lumbar spine (anterior or posterior in approach), the described vertebral implants for immediate fixation and staged stabilization leading to arthrodesis (bone fusion) of bone bodies may be used in a bone fracture or osteotomy to fuse together resulting bone bodies, and across one or more joints or articulations. Furthermore, the implants may be used in the lumbar, thoracic and cervical spine.

To facilitate fusion and healing of fractured bones, it has long, been known to utilize fixation plates and screws to hold together disunited bone bodies. Typically, the separate bone bodies are formed when a single bone fractures, requiring bone reunion. Plates are secured across a fracture region with screws, joining together the bone bodies. The plates hold the bone bodies together in proximate relation, facilitating bone growth and fusion there between. In this manner, the bone bodies are supported in close proximity, or in direct contact which facilitates fusion there between. For cases where it is impossible to fixture together bone bodies internally of a patient's skin, external fixation is used. For external fixation, threaded pins are rigidly secured into each bone body. The pins, which extend outwardly of a patient's skin, are fixtured together with an external fixation device, placing the bone bodies in adjacent proximate position to promote healing there between. However, this is not practical for certain joints such as joints formed between spinal vertebrae.

An early technique for achieving arthrodesis between adjacent bone bodies across a joint or articulation is the well known Cloward Technique for use in the human cervical spine. A solitary dowel of bone is tapped into place in a prepared circular bed that is smaller than the dowel of bone. The dowel acts as a wedge, distracting the surrounding soft tissues of the joint, and separating the bone bodies or vertebrae joined there along. The intervertebral disc substantially comprises the soft tissues of the joint. The dowel of bone is inserted, or wedged into place, providing its own stability by putting an annulus of the disc on stretch. Additionally, simple friction of the inserted dowel between adjacent vertebral bodies stabilizes axial dislocation. However, a second surgical procedure must be performed to extract or harvest the dowel of bone, substantially adding trauma to the procedure, increasing costs, as well as increasing the threat of infection to the patient. Alteratively, bank bone from human donors can be used, but bank bone is less osteogenic and may introduce infection, or even transmission of Acquired Immune Deficiency Syndrome (AIDS) or hepatitis. Furthermore, bone morphogenic protein, hydroxyapatite, or other bone stimulating material may be utilized. Additionally, there has been a need to ensure the implant remains axially secured which has lead to further developments.

As a step forward from the Cloward Technique, the Bagby metal dowel (U.S. Pat. No. 4,501,269) utilizes the same principle. A perforated cylindrical hollow implant is inserted between prepared surfaces across a vertebral joint. The inserted implant immediately stabilizes the joint by spreading the bony surfaces apart in wedged opposition to surrounding tissue. This initial stabilization is more substantial because a metal dowel, unlike a bone dowel, will not be absorbed or fatigue in use. Over time, fusion occurs through and around the implant which is filled with bone fragments. Use of the metal dowel eliminates the need for a second operation to harvest a dowel of bone. Bone fragments to be inserted in the implant are retrieved during preparation of the circular beds in each vertebra. Furthermore, such a metal implant avoids the disadvantage of having to use bone bank to obtain donor bone. The Bagby implant described in U.S. Pat. No. 4,501,269 has a smooth outer surface, interrupted only by numerous openings or fenestrations through which bone ingrowth and through growth can occur. Bone morsels or bone grafts are typically harvested when preparing the circular bed in each vertebra, after which they are placed into the fenestrated metal cylindrical implant. The Bagby implant is then driven or tapped into place in a manner similar to the placement of Cloward's Bone Dowel, which was solely directed for use in the cervical spine.

Improvements have also been made to "Cloward's Technique" wherein two dowel bone grafts are posteriorly inserted (Wiltberger's Technique) between adjacent lumbar vertebral bodies. Furthermore, threaded surfaces have been added to such bone grafts in order to keep the grafts in place (Otero-Vich German Application Number 3,505,567, published Jun. 5, 1986). More recently, a number of U.S. Patents have proposed combining the threaded features from threaded bone grafts with a metal implant, resulting in rigid threaded implant structures for placement between adjacent spinal vertebrae.

One threaded metal fusion implant disclosed in Michelson (U.S. Pat. No. 5,015,247) provides a cylindrical fusion implant having an outer diameter sized larger than the space between adjacent vertebrae to be fused. Threads provided on the exterior of the member engage the vertebrae to axially secure the implant there between. The implant has a plurality of openings configured along the cylindrical surface to promote bone ingrowth. However, the threads per se of the implant do not function as a fastener to fix together the adjacent vertebral bodies. Instead, the implant functions as a wedge, imparting a distraction force across the disc which stabilizes the articulation formed there between by stretching the annulus of the disc. In fact, the threaded implant relies solely on the annulus to provide stabilization between the vertebrae, in direct responsive to wedge-induced distraction created there between. Distraction of the annulus stabilizes the two vertebrae, enabling ingrowth to later occur within the implant. Therefore, through-growth and fusion (arthrodesis) occur between the adjacent vertebrae subsequent thereto depending on the immobilizing potential of an intact healthy annulus which may or may not be present. Therefore, there is a need to provide an implant that produces immediate fixation per se between bone bodies following insertion and independent of the annulus. Particularly for cases where the annulus structure is substantially or completely weakened or damaged at surgery of implantation, the wedge-effect of prior art threaded implants will not produce any distraction forces across the annulus. Also, when the implant is used to arthrodese and change angulation, a healthy annulus cannot be totally corralled to be placed on stretch. As a result, there is no form of stabilization or fastening between bone bodies sufficient to enable the occurrence of arthrodesis there between when the annulus is weakened or inadequate.

Another threaded implant disclosed in Ray (U.S. Pat. No. 5,005,104) provides a threaded fusion cage that is configured to be implanted in close adjoining pairs between adjacent vertebral bodies. Threads of adjacent cages are configured in overlapping relation when they are implanted. However, the fusion cages function only as wedges, imparting distraction forces across the annulus. The distraction forces immediately stabilize the intervertebral articulation by stretching the annulus of the disc immediately after implantation. Over time, the adjacent vertebrae fuse together. However, where a stretched annulus does not provide sufficient stabilization, initial early bone growth is seriously hindered, if not completely prevented. Furthermore, a stretched annulus can still allow slight motion.

For bone fusion to occur with any of the above devices, the invasion of new delicate blood vessels from the adjacent healthy bone is necessary for the creation of new living interconnecting bone. Where complete stabilization does not occur instantaneously upon implantation, motion can disrupt the in growth of delicate blood vessels. Disruption of the vessels then restricts or even prevents bone healing there between. The same problem occurs with any of the above mentioned implant techniques, including the threaded techniques of Otero-Vich and Michelson. Even when the annulus is completely on stretch, the threads per se of these constructions do not function in the manner of conventional screws, extending through one object and into another. Namely, they do not function to fasten together adjacent bodies by coaction of the thread with each body. Alternatively, they do not fasten together bodies by action of the thread with one body, and action of a fastener head with the other body. Instead, the threads merely act as a series of ridges that engage with each adjacent bone body, while the implant body functions as a wedge. The implant distracts apart the vertebral bodies which stretches the annulus, and stabilizes the articulation as a consequence thereof, while the thread functions solely to prevent axial dislodgement.

A further area of prior art relates to implants having surface features that enable bony ingrowth to occur. For example, beads of titanium have been provided on the stems of hip implants to form such features. Ingrowth by a bone bed with the structural features occurs some time after implantation. Therefore, fixation is not immediately present as a result of the surface features, and some other fixation must be relied upon until ingrowth occurs. With the exception of the Cloward Bone Dowel and Otero-Vich, the above-mentioned vertebral body implant devices incorporate fenestrations or openings that tend to facilitate bony ingrowth into the metal spinal implants.

Additionally, Lin et al. (U.S. Pat. No. 4,778,469) teaches a surface construction of a space occupier having a pattern for tissue ingrowth in the surface of an implant. Tapered posts having undercuts are provided along a surface of a hip implant. Subsequent to implantation, physiological bone ingrowth occurs within the undercuts, helping to fix the implant within the bone. However, this construction does not enable immediate fixation via the undercuts. Instead, it relies upon physiological bone ingrowth which takes time to occur. Therefore, other mechanisms must be relied upon to maintain implant fixation within the bone prior to ingrowth. Such is also the case with the previously mentioned vertebral implants.

Therefore, there is a present need to provide implant devices that fasten bone bodies together directly upon implantation. There is also a need to provide such a device that facilitates staged stabilization, ultimately leading to bone fusion there between. The final stage of bone fusion through and around the implant substantially eliminates any need for the implant to maintain the fusion, thus allowing the bone union to provide primary support there between, i.e. the implant can be removed without reversing the arthrodesis in such cases as chronic infection. Furthermore, there is a need to provide such a device for fixing bone bodies together across an articulation or joint (arthrodesis). Particularly, this need exists where soft tissues of an articulation have deteriorated to such a condition that distraction across the articulation will not produce stability. For example, prior art devices (including the above-mentioned vertebral body implant devices) cannot stabilize an articulation by inducing a wedging apart, or stretching of an annulus where the annulus is weakened or absent. Therefore, interim stability cannot be imparted between adjacent vertebrae at the time of surgery. Such interim stability is needed for successful fusion. As a result, ingrowth and through growth needed to fuse the bone bodies together for long-term stability is less likely to occur on a routine basis.

BRIEF DESCRIPTION OF THE DRAWINGS

Preferred embodiments of the invention are described below with reference to the following accompanying drawings.

FIG. 1 is a perspective view of a vertebral structure showing a pair of vertebral interbody implants embodying this invention, one inserted and the other positioned for insertion. A solitary implant (not shown) may be used in certain cases;

FIG. 2 is a side elevational view illustrating the vertebral interbody implant of FIG. 1;

FIG. 3 is a leading end view taken generally on line 3—3 of FIG. 2;

FIG. 4 is a trailing end view taken generally on line 4—4 of FIG. 2;

FIG. 19 is a front elevational view of the device of FIGS. 15 and 18 after removal of the midmost vertebra, insertion of a medial cruciate baffle, and prior to closure of the surgical wound.

DETAILED DESCRIPTION OF THE PREFERRED EMBODIMENTS

Figure 5:
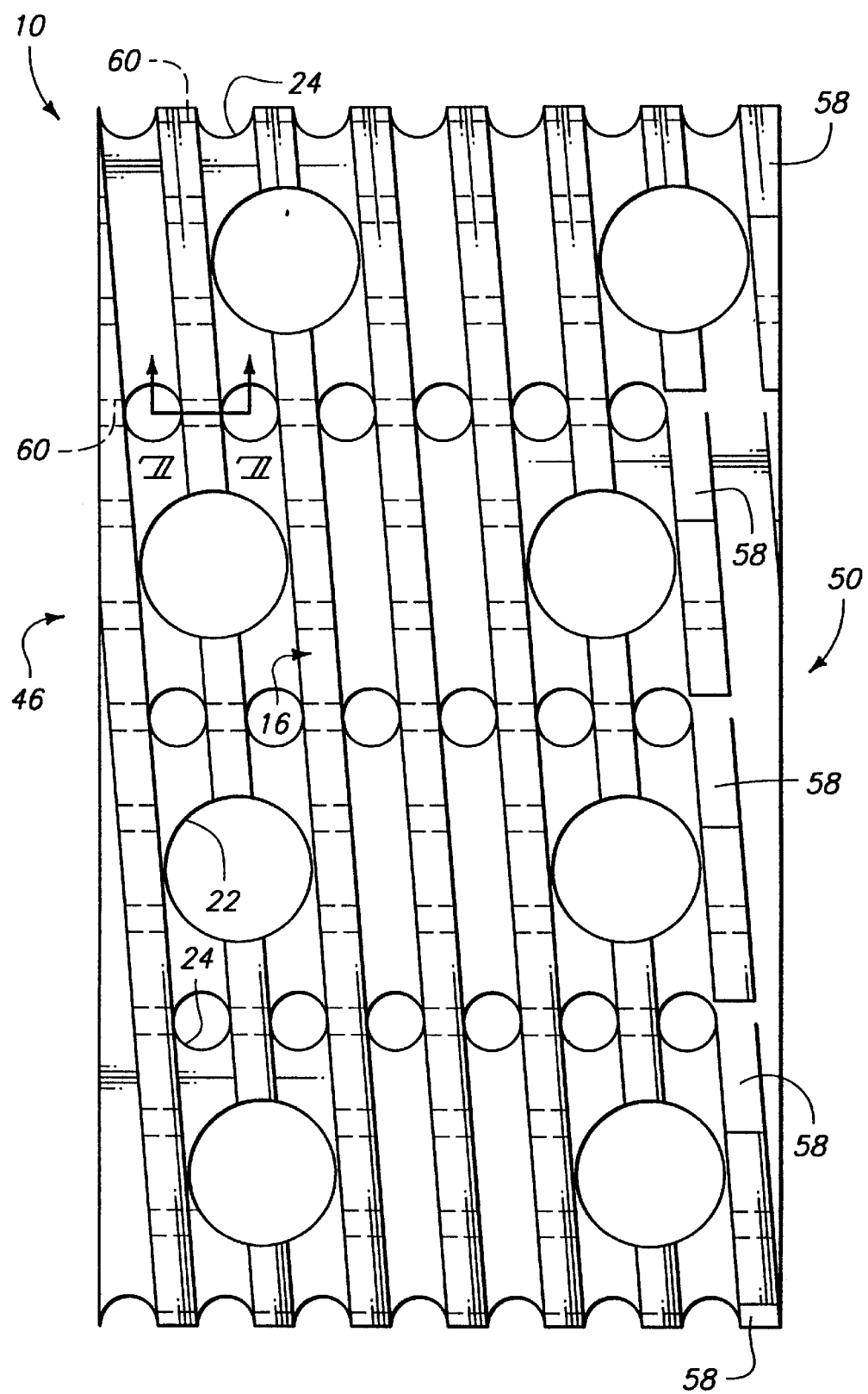
FIG. 5 is an unrolled plan view of the outer peripheral surface of the vertebral interbody implant of FIGS. 1–3.

This disclosure of the invention is submitted in furtherance of the constitutional purposes of the U.S. Patent Laws "to promote the progress of science and useful arts" (Article 1, Section 8).

In accordance with one aspect of the invention, a bone joining implant is engaged between a pair of bone bodies to be joined. The implant has a rigid, implantable base body with an outer surface having at least one bone bed engaging portion. The outer surface engages with a bone bed prepared in each bone body to be joined. One or more splines are provided by the bone bed engaging portion. The spline is constructed and arranged to extend outwardly of the implant body. Furthermore, the spline has an undercut portion configured to engage in interlocking relation with a bone bed provided in each of the BONE BODIES to be joined.

In accordance with another aspect of the invention, a vertebral interbody implant is engaged between a pair of adjacent vertebrae to be joined. The implant has a body sized to be received between a pair of adjacent vertebrae to be joined. The body forms an outer surface having at least one bone bed engaging portion configured to be engaged with a bone bed on each of a pair of vertebrae to be joined. At least one thread is formed by the bone bed engaging portion that extends radially outward of the body in a generally helical configuration. The thread is configured to engage in assembly with each adjacent vertebra. Furthermore, the thread has an undercut portion provided on a radial inner portion for engaging in interlocking relation with a bone bed in each vertebra. In assembly, the implant engages in interlocking relation with a pair of vertebrae joined there along.

In accordance with yet another aspect of the invention, a vertebral bridging implant is received about a vertebral body to be removed by a corpectomy. An implantable body on the implant has an inner dimension sized to be received about the vertebral body to be removed. An outer dimension on the body is sized to be received between a pair of vertebrae to be joined adjacent thereto. The body has an outer surface with a bone bed engaging portion configured to be engaged with bone beds on each vertebra to be joined. An undercut spline extends outwardly of the body, provided by the bone bed engaging portion. In assembly, the spline mates in interlocking engagement with the bone bed of each vertebra, joining the non-adjacent vertebrae in interlocking relation.

A preferred embodiment bone joining implant in accordance with the invention is first described with reference to FIGS. 1 through 11. Such an implant is described further below with respect to a threaded vertebral interbody implant having an undercut thread portion. The undercut threaded implant is designated in FIGS. 1–11 generally with numeral 10. A pair of implants 10 are depicted in this implementation. Alternatively, a single implant could be used. As shown in FIG. 1, such comprises a rigid, cylindrical base body 12 having a helically configured spline or thread 14 configured on an outer surface 16 of body 12. A central chamber 18 is formed within body 12 for receiving bone graft material 20 therein. Large and small fenestrations 22 and 24 extend through surface 16 into chamber 18 for facilitating bony ingrowth and through growth therethrough. Thread 14 has an undercut 26 which meshes in assembled engagement within bone beds 28 and 30 in vertebra 32 and 34. Each bed 28 and 30 forms complementary female threads for receiving the undercut thread in interlocking engagement there along. For purposes of this disclosure, a spline shall include any thread, web, strip, ridge, or portion of material formed from continuous material, or broken into fragments (interrupted).

As shown in FIG. 1, vertebrae 32 and 34 comprise neighboring bone bodies of a vertebral column 36. A resilient articulation 38 or joint is formed between vertebra 32 and 34 by a disc 40 extending there between. Anatomically, the disc is made up of a central nucleus pulposus and an outer encircling annulus. The annulus and nucleus pulposus are composed of laminae of fibrous tissue and fibrocartilage. The nucleus pulposus, located at the center of the disc, comprises a soft, pulpy, highly elastic substance. The annulus is formed from laminae of fibrous tissue extending in criss-crossing fashion to encircle the nucleus pulposus. Additionally, the intervertebral disc is adherent, by its cephalad and caudad surfaces, to a thin layer of hyaline cartilage that covers the top and bottom surfaces of adjacent vertebrae. In a healthy patient, adjacent vertebra 32 and 34 are spaced apart by the disc 40. However, degenerative disc disease and localized trauma can cause degradation or complete loss of the soft tissue components between neighboring vertebrae. For example, the annulus can partially or completely tear which can seriously degrade the structural condition of the articulation. Additionally, fluid can escape from the nucleus pulposus. When any of the above happens, vertebrae 32 and 34, loaded by the normal weight bearing of a patient, are pressed into closer adjoining positions, which can result in pinching of nerves that extend from between vertebrae of the spinal column (not shown).

Therefore, there is a need to recover the disc spacing provided by a normal healthy disc 40 by way of inserting implants 10. Furthermore, there is a need to provide implants 10 with a fixation that instantly interlocks adjacent vertebra 32 and 34 together upon being implanted. Furthermore, there is a need for such an implant 10 that facilitates staged stabilization resulting in arthrodesis to occur between the vertebral bodies, following initial implantation.

As a result, implant 10 can be inserted, preferably in left and right laterally positioned pairs, between adjacent vertebrae of patients who have bad, ruptured or degenerative discs. A solitary implant may also be used in chosen cases. For example, the implant can be axially oriented anterior to posterior, or even laterally. In summary, implants 10 are adapted for implantation between prepared bony surfaces or beds 28 and 30 of articulation 38. A typical implantation might involve placement of one or more implants 10 as required in order to stabilize and fix the joint during bone ingrowth and through-growth of the implant structure. Bone growth is also accomplished outside of and surrounding the implant.

Preparation of bone beds 28 and 30 is performed according to well known techniques in the art, with the exception that presently available tapping devices are modified according to one implementation of this invention. During a surgical procedure, a prepared and exposed vertebral column 36 receives a hollow guide tube (not shown) having teeth at its lower end. The tube (or sleeve) is mated with its lower end engaging across articulation 38, wherein the teeth engage vertebrae 32 and 34. A drill (not shown) is then guided down the tube in order to drill a pilot hole between the vertebrae, imparting the general cutout configuration to beds 28 and 30. Subsequently, a preliminary tapping device is received through the tube into the pilot hole where female threads of rectangular cross section are cut into beds 28 and 30. The female threads are undersized in width, requiring further self-tapping by the implant during insertion. Alternatively, the tapping device can be configured to cut female threads having an undercut cross section sized and configured to conform with the undercut threads 14 on implant 10. For the case where threads are cut with a rectangular cross section, implant 10 has self-tapping features provided by thread 14. The self-tapping features enlarge the radial outermost portion of each complementary corresponding female thread provided by beds 28 and 30, respectively.

An additional benefit is provided when implant 10 is self-tapped into an undersized female thread in each bone bed 28 and 30. Namely, in practice it proves difficult to maintain precise spaced apart positioning of vertebrae 32 and 34 following drilling of beds 28 and 30. Therefore, even slight variations in spacing produce a misfit between the outer surface of implant 10 and each bed 28 and 30. However, where implant 10 has self-tapping features, the self-tapping mitigates any slight misfit condition by at least partially reforming the beds 28 and 30 during insertion. Furthermore, a laterally positioned pair of implants 10 proves difficult to implant with a perfect fit up between the implants and the bone beds. Typically, a first site is prepared and one implant is inserted, after which a second site is prepared and a second implant is inserted. However, the bone beds at each site tend to shift as each implant is inserted since the pair of implants are not inserted simultaneously.

FIG. 2 illustrates undercut threaded implant 10 in a side elevational view corresponding to a preferred rotationally positioned and implanted configuration within a patient. Large fenestrations 22 are formed along a pair of perpendicular axes that substantially bisect vertical and horizontal planes of a patient receiving the implant. Large fenestrations 22 are sized and located to allow for reorganization or hardening of bone by maturity after initial bone healing. FIG. 3 clearly illustrates such a configuration. In this manner, top most or cephalad and bottom most or caudad portions of implant 10 present an outer surface that is void of any large openings or fenestrations. Such a surface substantially enhances load bearing there along, following implantation. However, such placement of large fenestrations 22 still provides a significant path for subsequent ingrowth and through growth between adjacent vertebral bodies receiving implant 10. Additionally, small fenestrations 24 provide paths for ingrowth and through growth. Furthermore, the above-described orientation and size of fenestrations 22 is well suited for staged fusion and subsequent bone remodelling, leading to structurally enhanced fusion between vertebrae 32 and 34.

Implant 10 of FIG. 2 is depicted with a plastic end cap 42 that mounts in engagement with an opening 44 formed in a trailing end 46 (as shown in FIG. 4). End cap 42 is optionally mounted to implant 10 when performing a bilateral implantation by way of a posterior approach. Such a posterior surgical approach presents a special concern; namely, that the dura of the spinal cord might rub against the driving or trailing end 46 of implant 10. Therefore, end cap 42 is secured in opening 44 to protect the spinal cord, following implantation of implant 10 and the inserted bone graph material therein.

Additionally, small fenestrations 24 are formed in implant 10. The small fenestrations 24 extend substantially throughout the walls of the cylindrical implant. Small fenestrations 24 offer avenues of ingrowth of bone between vertebrae 32 and 34, which is stimulated by bone graft material placed within central chamber 18 during implantation. In this manner, fenestrations 24 serve to facilitate earlier and more thorough ingrowth of bone within implant 10. Furthermore, fenestrations 24 enhance overall through growth of bone through implant 10.

Large fenestrations 22 are preferably sized and configured to interrupt no more than one complete width of thread 14. Hence, the total amount of interlocking of undercut thread 14 with bone beds 28 and 30 is optimized. According to this construction, fenestration 22 extends substantially between a first and a third adjacent portion of helically wound thread 14, while interrupting a second, or middle portion. A taper 56, also provided along end 50 reduces the height of thread 14 substantially to a diameter of base body 12, immediately adjacent leading end 50. Placement of fenestrations 22 in close proximity with leading end 50 tends to interrupt thread 14, at least partially providing a self-tapping feature there along. Furthermore, fenestrations 22 allow for self depositing of bone chips during the self tapping process of implant 10. Bone chips are delivered into the large and small fenestrations 22 and 24, as well as into central chamber 18 during self tapping of the implant. Such bone chips supplement bone graft material 20 that is packed into the implant, which together encourage the early process of arthrodesis. These delivered bone chips produced in self tapping remain alive since they never leave the patient's body. Therefore, they tend to be more osteogenic than if they were nonviable.

As shown in FIG. 2, fenestrations 22 only partially provide for complete self-tapping. Therefore, cut-out portions 58 are also formed along thread 14 in order to add further self-tapping features. Additionally, thread 14 within the region of taper 56 also forms an undercut 26 so that progressive formation of complementary corresponding under cut female threads can be formed wit hin bone beds of adjacent vertebrae receiving the implant.

Alternatively, fenestrations 22 can be provided immediately adjacent to leading end 50, eliminating the need for cut-out portions 58 altogether when providing self-tapping features on implant 10. For cases where female threads 66 are preformed into beds 28 and 30 with undercut, there is little or no apparent need for such self tapping features. In such cases, fenestrations 22 can be placed anywhere along implant 10, and cut-out portions 58 (FIG. 5) can be eliminated (i.e. No other self-tapping needed).

Referring to FIG. 3, leading or advancing end 50 of implant 10 is clearly shown. Cut-out portions 58 can be clearly seen in this view. Additionally, taper 56 progressively decreases the height of thread 14 as it extends helically toward leading end 50, until it merges into base body 12. Furthermore, a plurality of axially extending through holes 60 cut through thread 14 are clearly shown. Through holes 60 facilitate early stage ingrowth of bone with implant 10 following implantation. As shown in FIG. 3, through holes 60 are also formed in thread 14 in the region of taper 56, thereby interrupting thread 14 in the region of taper 56 so as to impart even further self-tapping features there along. Alternatively, through holes 60 can be omitted in the region of taper 56.

Opening 48 in leading end 50 is sized smaller in diameter than an inner wall 62 of the implant base body 12, as shown in FIG. 3. In this manner, a structure enforcing bulkhead is provided at the leading end. Additionally, a similar centrally positioned bulkhead 54 is also provided intermediate of the advancing and driving ends 50 and 46, respectively, within central chamber 18. Central bulkhead 54 has an oval slot 52 extending completely therethrough for mating with a fingered end of a driver (not shown). The slot mates with the finger, allowing torquing of threaded implant 10 into the bony beds of adjacent vertebrae. Typically, such a driver construction is required in order to impart large forces necessary to insert implant 10 into the lumbar region of a patient's spine. Alternatively, a driver can be configured to mate with trailing end 46 via a plurality of dowels on the driver. The dowels are received in complementary corresponding receiving holes (not shown) of the implant there along. Such a construction is well suited to an implant that is sized to be received also in the cervical region of the spine where less torque is required to insert implant 10 therein.

A further alternative construction calls for formation of an oval slot (similar to slot 52 of FIGS. 3 and 4) in place of opening 44 in trailing end 46. Provision of the slot in the trailing end will enable driver engagement suitable to insert as well as remove the implant. Hence, the same tool can be used to remove the implant. Furthermore, the leading end can have a similar slot, allowing for surgical removal of an implant where a posteriorly inserted implant needs to be removed from the anterior for surgical reasons.

As shown in FIGS. 3 and 4, axially extending through holes 60 are provided in implant 10 in locations that correspond with the vertical and horizontal planes of a patient receiving the implant. Additional through holes 60 are provided between the holes positioned along the vertical and horizontal planes, enabling further initial ingrowth there along. For holes 60 that are positioned in locations along the vertical and horizontal planes, such holes are provided adjacent small fenestrations 24 which further facilitates ingrowth and through growth there along.

As shown in FIG. 4, trailing or driving end 46 has opening 44 which is sized similarly to opening 48 in leading end 50 (of FIG. 3). In this manner, opening 44 is sized smaller than inner wall 62, forming an enforcing flange from a portion of trailing end 46 extending there along. Additionally, FIG. 4 illustrates termination of undercut thread 14 along trailing end 46 of implant 10. Preferably, axially extending through holes 60 are machined through the helically extending thread 14 progressively from the trailing end 46 toward the leading end 50. In this manner, a drill bit received there along to cut holes 60 can be axially advanced, short of drilling through thread 14 in the region of taper 56 if such a construction is so desired.

According to FIG. 5, outer surface 16 of implant 10 is shown in an unrolled plan view to better depict layout of thread 14, fenestrations 22 and 24, through hole 60, and self-tapping cutout portions 58. The particular layout leads to the various above described benefits. Various alternative layouts can be readily envisioned for thread 14, fenestrations 22 and 24, through hole 60 and self-tapping cutout portions 58, and fall within the claimed subject matter of this invention. Additionally, any one or more of such features can be eliminated, with the exception of an undercut spline, or thread, yet still remain within the claimed scope of this invention.

Figure 6:
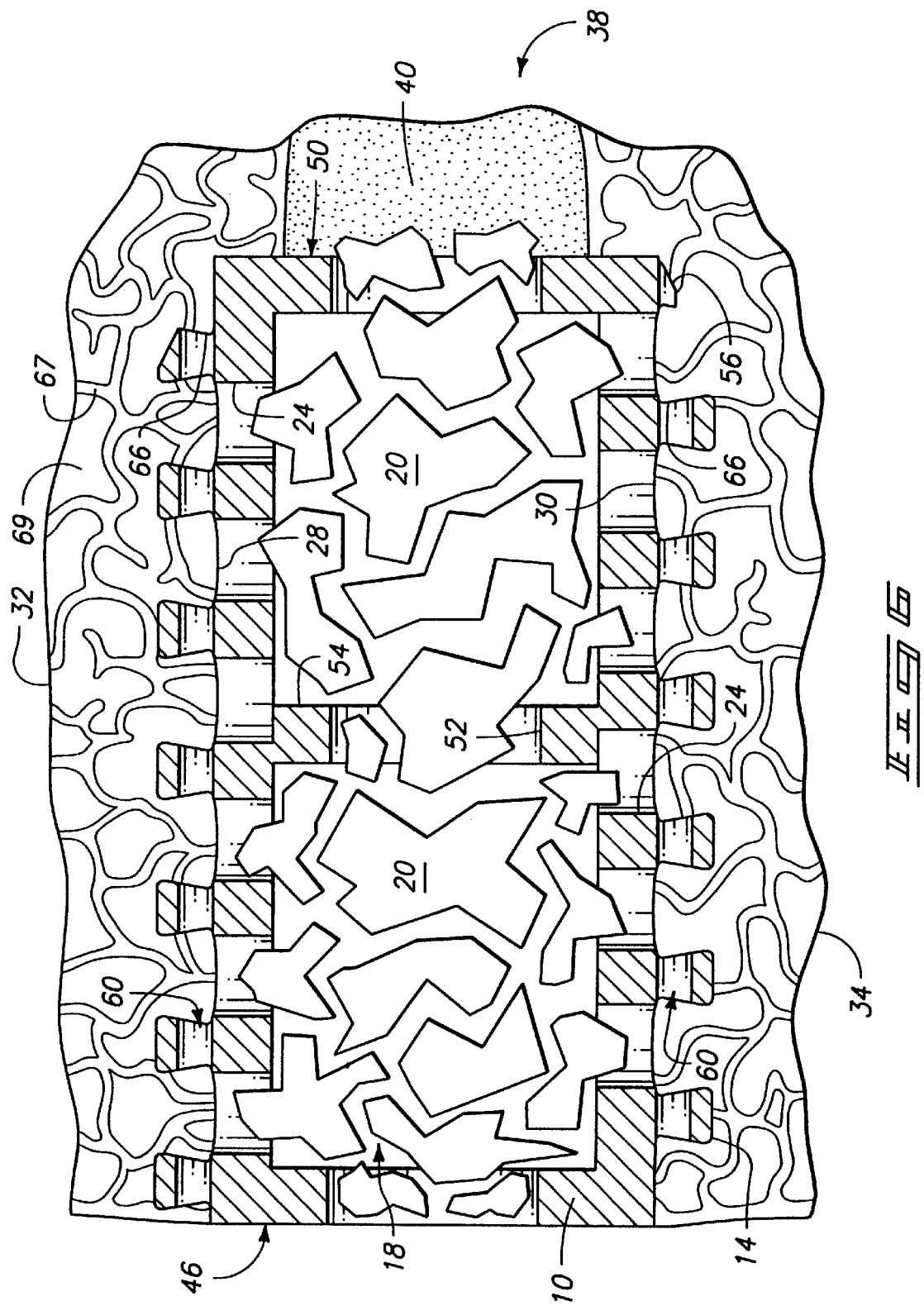
FIG. 6 is a cross sectional view taken generally on line 6—6 of FIG. 3 of the vertebral interbody implant immediately after implantation.

FIG. 6 depicts implant 10 of FIGS. 1 through 5 immediately after implantation within prepared bone beds 28 and 30 of vertebrae 32 and 34, respectively. According to the depicted implantation of FIG. 1, bone beds 28 and 30 are prepared by forming female threads 66 therein, prior to receiving implant 10. Subsequently, implant 10 is inserted by threading in into the beds with a driver.

As shown in FIG. 6, a bore 68 is cut into vertebrae 32 and 34 (partially shown) by progressively enlarging the bore with a series of reamers received through a hollow guide tube (not shown). Subsequently, a tap is inserted through the guide tube to cut thread 66 into each vertebrae 32 and 34. In the embodiment of FIG. 6, female threads 66 are cut to have a square cross-sectional configuration, after which the self cutting features of thread 14 enlarge the square female threads during insertion of the implant. Hence, complementary corresponding undercut female threads 66 are formed that are configured to receive undercut thread 14 in snug and inter-locking engagement there along. By pretapping a square (or some other closely configured) thread into the bone bodies, the self tapping implant 10 can complete the tap, which interlocks the implant with each bone body. In this manner, implant 10 when inserted, interlocks vertebrae 32 and 34 together immediately upon implantation, instantly stabilizing articulation 38. Subsequently, bone ingrowth and through growth occurs via through hole 60 and fenestrations 22 and 24, by way of enhanced development via bone grafts 20 packed into central chamber 18. Therefore, with such a construction, the prior art reliance on a wedging effect to stretch disc annulus 40 in order to stabilize the joint until bone fusion occurs there between is eliminated. However, it is still desirable to prepare beds 28 and 30 such that distraction occurs across disc 40, further stabilizing articulation 38 there between. Additionally, a bone distractor can also be used during preparation of bone beds and implant insertion to pull apart the vertebrae, putting the disc annulus on stretch in the final implanted configuration.

Figure 7:
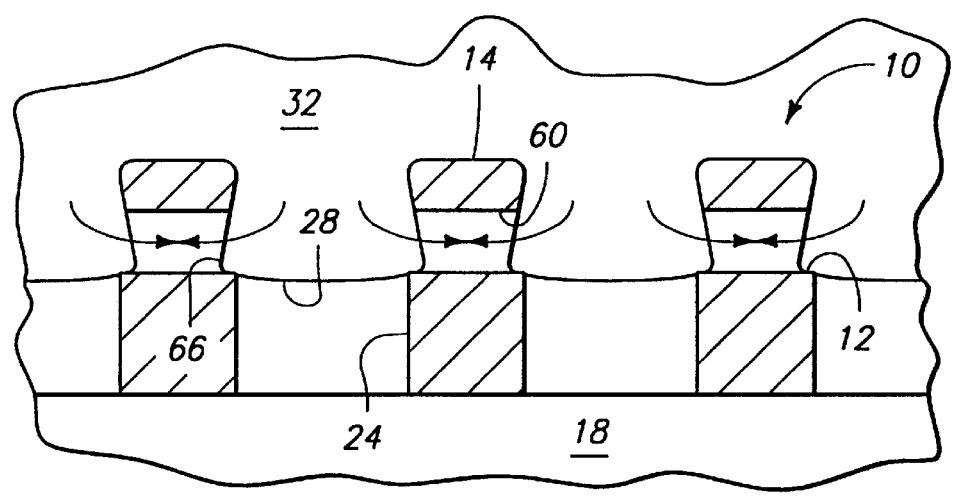
FIG. 7 is a fragmentary and enlarged cross-sectional view taken generally on line 7—7 of FIG. 5 and shows initial surface through growth diagrammatically.
Figure 9:
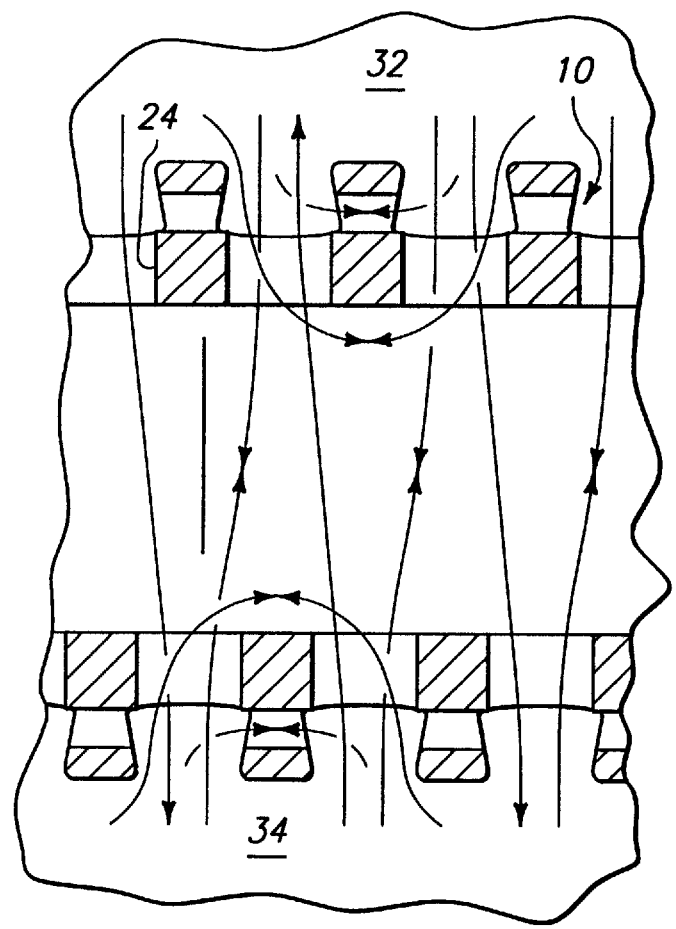
FIG. 9 is a cross sectional view corresponding to that of FIG. 8, but taken later in time and illustrating advanced bone through-growth (diagrammatically) beyond surface growth and ingrowth of FIGS. 7 and 8, and illustrates bone joining and connecting vertebrae.
Figure 10:
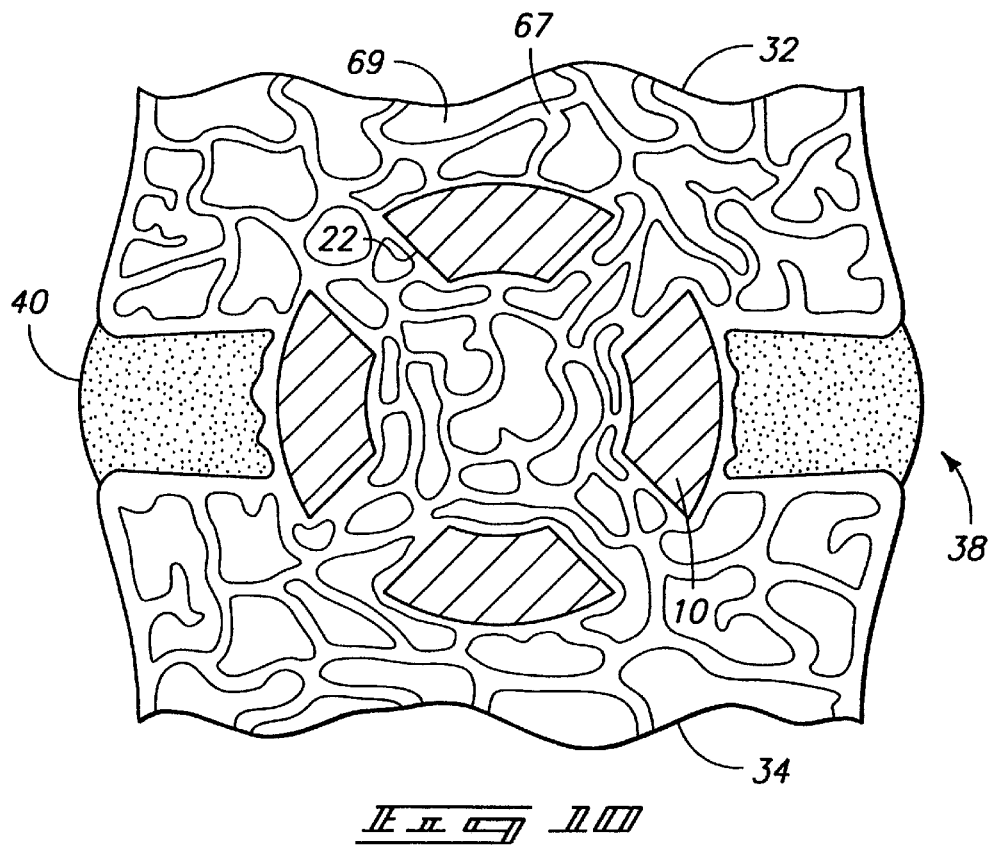
FIG. 10 is a cross sectional view taken generally on line 10—10 of FIG. 2 illustrating bone through-growth at the same time as that depicted in FIG. 9, but in histologic detail.
Figure 11:
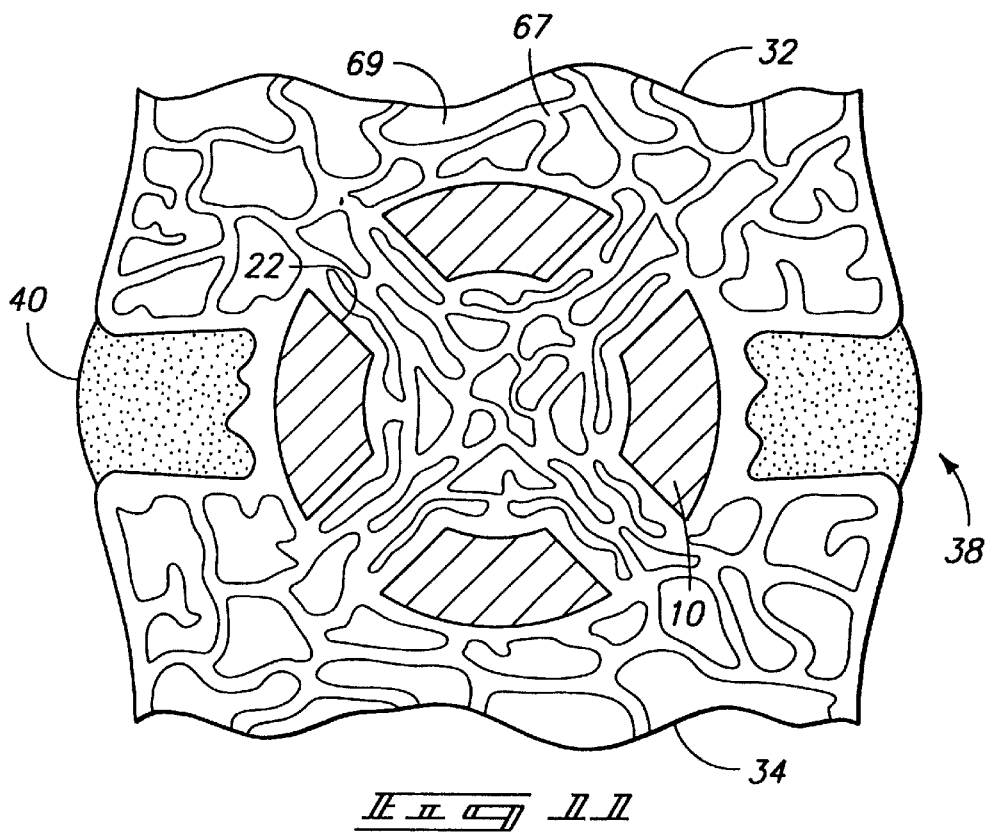
FIG. 11 is a cross sectional view corresponding to that of FIG. 10, but taken later in time and illustrating bone remodelling.
Figure 12:
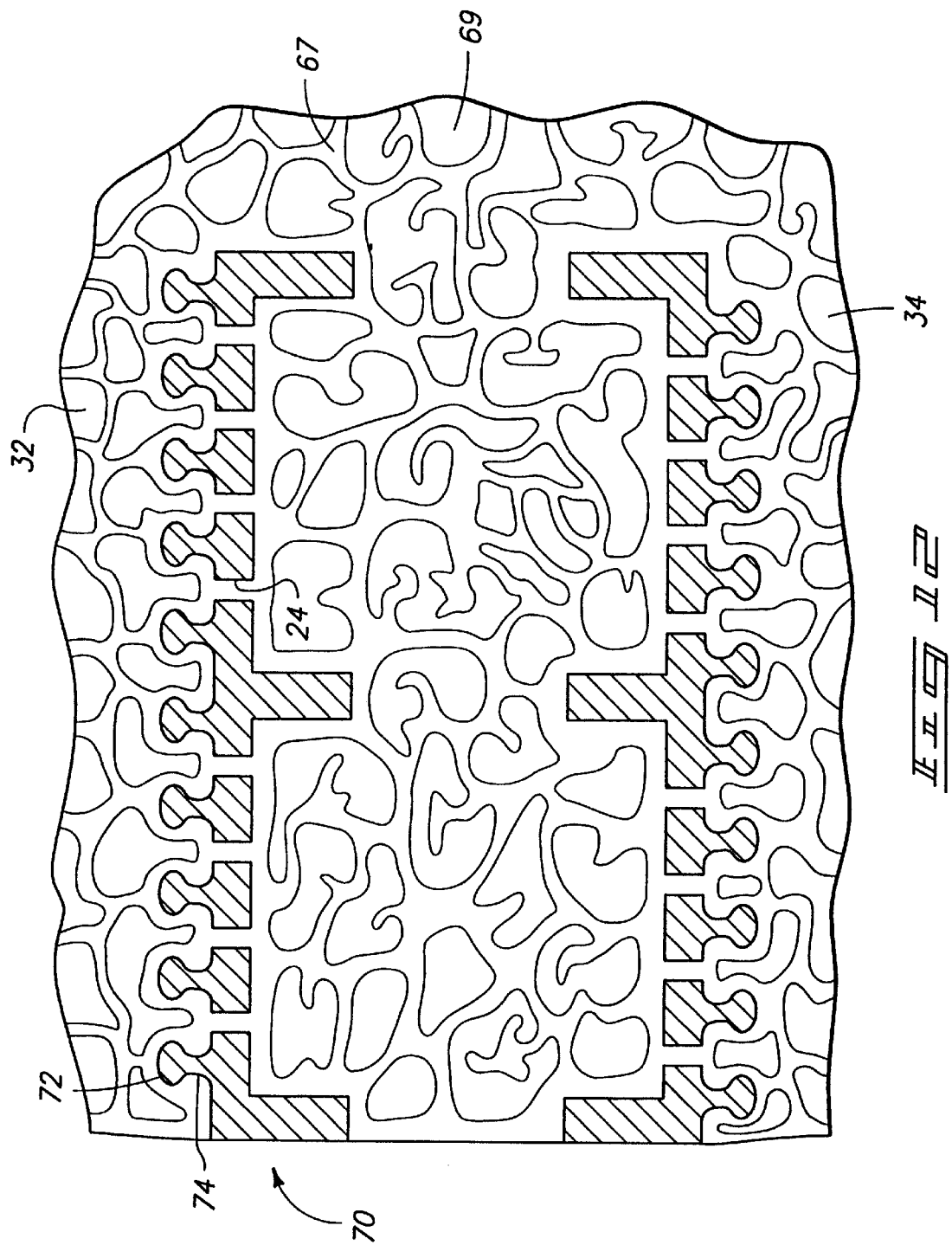
FIG. 12 is a fragmentary and enlarged centerline sectional view depicting a vertebral interbody implant having an alternative undercut thread construction with bony through growth.

Implant 10 according to the construction of FIGS. 1–5 facilitates staged stabilization and a bone fusion between vertebrae 32 and 34. FIG. 6 illustrates the first stage of stabilization across articulation 40, wherein undercut thread 14 interlocks in female threads 66 of each vertebra, imparting instant fixation and frictional stabilization there between. Furthermore, annulus 40 further cooperates with the implant to control distraction. A second stage of stabilization is depicted in FIG. 7, wherein new bone from the living female bone threads 66 through grows into through hole 60. A third stage of stabilization is depicted in FIG. 7, wherein bone grows through small fenestrations 24 enjoins with bone growing from the same vertebra through an adjacent fenestration, and can further incorporate a portion of bone graft material contained within the implant. Furthermore, such ingrowth can occur through large fenestrations (not shown). A fourth stage of stabilization is depicted in FIGS. 9 and 10, wherein initial bone growth occurs through the implant, connecting vertebrae 32 and 34. Such a condition forms an initial bone fusion. A fifth and final stage of fusion is depicted in FIGS. 11 and 12, wherein the fused bone of FIG. 11 has reorganized according to Wolff's law. The trabeculae relocate through large fenestrations 22 to form a mature strengthening of the trabeculae. Additional reorganization can be facilitated outside of the implant by providing bone graft material thereabout at the time of implantation. Such a staged stabilization enables instant fixation between vertebrae 32 and 34, after which the articulation 38 is stabilized and stress protected by shifting load-bearing from the implant to newly formed and reorganized bone occurring there between. For cases where staged stabilization and bone fusion is not allowed to occur, stress protection osteopenia can result from normal physiologic stress through the bone being removed via the implant, which can cause localized osteoporosis.

FIG. 7 is a fragmentary and enlarged cross-sectional view taken generally on line 7—7 of FIG. 5 illustrating an initial stage of bone ingrowth with arrows. Bone ingrowth occurs early on through axially extending through holes 60 due to their short length and proximity to healthy developed bone in living beds 28 and 30. Since holes 60 are cut in thread 14 immediately adjacent base body 12, holes 60 are shallow, and bone growth from living bone beds 28 and 30 need only progress a short distance in order to extend completely through holes 60. Therefore, early through growth can occur through holes 60, which further fixes and stabilizes implant 10 to vertebrae 32 and 34. Such early ingrowth within holes 60 provides fixation above and beyond that provided by the interlocking fit of undercut thread 14 within female threads 66. Additionally, through growth of bone into holes 60 prevents any loosening or "unscrewing" of implant 10 from within female threads 66 of beds 28 and 30. Holes 60 impart a cotter-pin effect, locking implant 10 within threaded beds 28 and 30. A typical time for complete through growth of holes 60 in an active and healthy patient ranges from about two weeks to four weeks.

Figure 8:
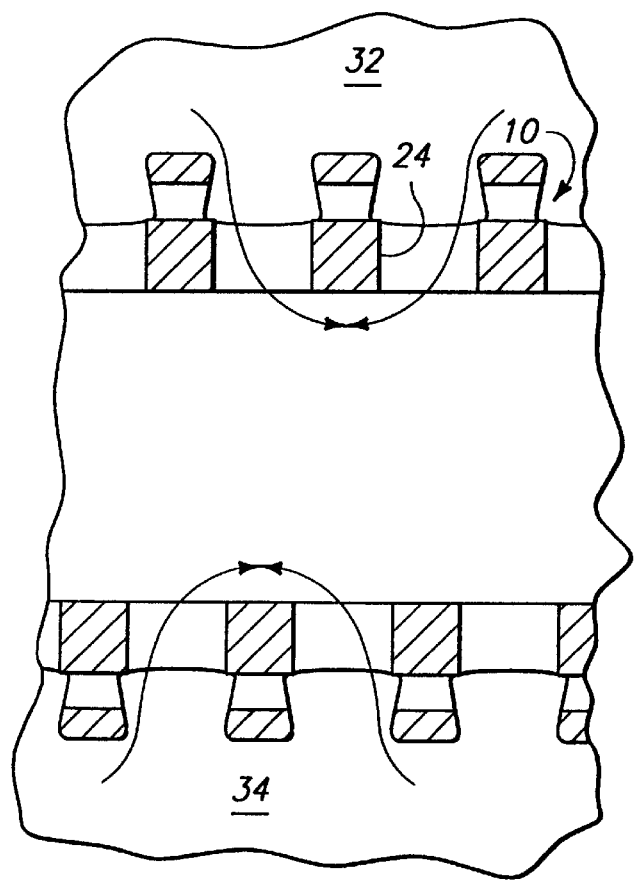
FIG. 8 is a cross sectional view taken generally on line 8—8 of FIG. 4 of the vertebral interbody implant subsequent to implantation and illustrating bone in-growth (diagrammatically) including the bone grafts with interlocking.

FIG. 8 schematically depicts a cross-sectional view of implant 10 taken generally on line 8—8 of FIG. 4. The arrows of FIG. 8 schematically represent bone ingrowth in the form of arrows that occurs through adjacent fenestrations 24 by way of the same vertebral body 32 or 34. The ingrowth through fenestrations 24 of FIG. 8 occurs somewhat later in time than the ingrowth through holes 60 of FIG. 7. The typical time for through growth is from one month to 3 months. Ingrowth by way of fenestrations 24 further ensures fixation of implant 10 to vertebrae 32 along a top portion, and to vertebrae 34 along a bottom portion. At this stage of stabilization, implant 10 still holds vertebrae 32 and 34 together in structural relation. Furthermore, the ingrowth depicted in fenestrations 24 in FIG. 8 also occurs through fenestrations 22 (not depicted).

FIG. 9, taken later in time than FIGS. 7 and 8, depicts complete through growth (arthrodesis) of implant 10 by healing bone following earlier ingrowth. According to FIG. 9, a simplified and somewhat schematic cross-sectional configuration shows large fenestrations 22 and omits small fenestrations 24 for clarity. Furthermore, through growth is depicted in the form of arrows extending between vertebra 32, along a top portion, and vertebra 34, along a bottom portion. At this stage of bone fusion, bone graft material 20 that was initially placed in chamber 18 has fused with healing bone from vertebrae 32 and 34. The fused bone provides a continuous path of structural bone there between.

Furthermore, an additional pathway of bone not depicted in FIGS. 7–9 is bone growth outside of and around the implant. Such an initial bone fusion tends to have a somewhat random or directionally uniform bone cell orientation. The bone cells lack any optimized or reorganized structural orientation there through, other than that dictated by passageways that originally allowed for the bone growth. As shown in FIGS. 9 and 10, the general characteristics of such initial bone fusion lacks any substantial reorganization. Hence, bone cell geometry has not been structurally oriented to optimize structural loading.

FIG. 10 depicts histologic bone cell geometry in greater detail, corresponding in time to that depicted in FIG. 9. Lacunae and canals or voids 69 are formed between the bone 67. The lacunae represent the voids between the bone where soft tissue, blood vessels, and fatty deposits reside.

According to FIG. 11, reorganization of fused bone material through implant 10 is shown generally occurring between vertebrae 32 and 34. The fused bone consists of bone ingrowth and through growth of holes 60, fenestrations 22 and 24, and openings 44 and 48. According to this simplified schematic representation depicting fenestrations 22, the bone cells of FIG. 11 have remodeled so as to optimize the substantially vertical loading. Such loading represents the vertical weight bearing that a patient will impart on the implant system as surgically placed in the configuration of FIGS. 10 and 11. In such a manner, bone cells have remodeled to form a definite elongated configuration extending between vertebrae 32 and 34 through fenestrations 22. Such remodelled bone through growth can be seen between fenestrations on same sides of a patient, occurring from cephalad to caudad, as well as between fenestrations along a diagonal configuration of the patient, from cephalad to caudad. The large fenestrations 22 allows nature (by Wolff's law) to locate and strengthen large trabeculae. The latter also occurs around the outside of the implant between the vertebrae, as shown in FIGS. 10 and 11.

FIG. 12 depicts an alternatively constructed bone joining implant 70 implanted between vertebrae 32 and 34, but in a totally fused together and remodelled bone configuration. Such a final state of fusion transfers loading through the remodelled bone resulting from arthrodesis and remodelling. Hence, the need for implant 70 to carry load is greatly diminished, or even eliminated. In some cases, the implant can be subsequently removed where arthrodesis has occurred along the outside of the implant without reversing the bone fusion. According to FIG. 12, bone union can be clearly seen around the outside of the implant.

Implant 70 of FIG. 12 has a modified form of thread 72 having an undercut 74 formed by enlarging the radial outermost portion of thread 72. Alternatively, a bead having a cylindrical, oval, or semi-circular cross-sectional configuration can be affixed to the base to form thread 72. Fenestrations 24 are also depicted on implant 70. Additionally, large fenestrations 22 (not shown) substantially similar to those depicted in the device of FIGS. 1 through 11 are also present.

Figure 13:
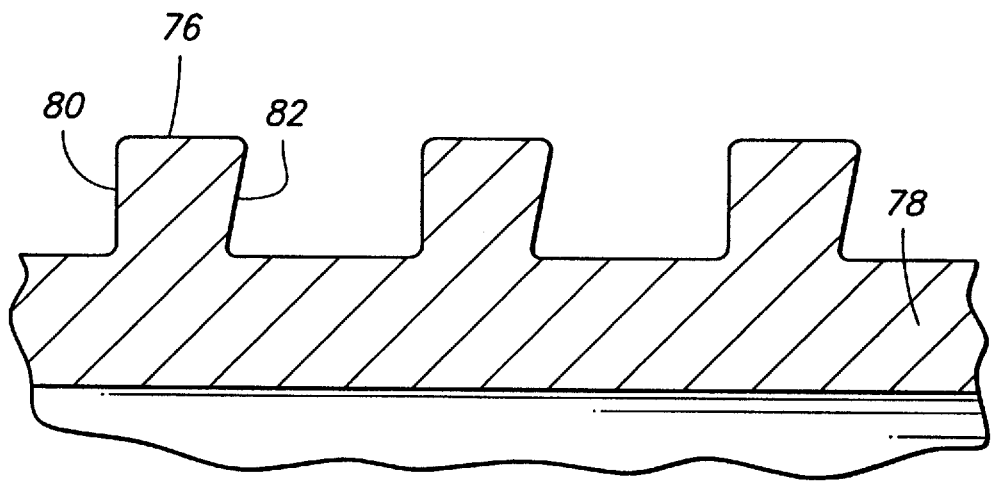
FIG. 13 is a fragmentary and enlarged centerline sectional view depicting a vertebral interbody implant having another alternative undercut thread construction.

FIG. 13 is a fragmentary and enlarged center line sectional view of a further alternative construction for a thread 76 on implants 78 substantially similar to that depicted in FIGS. 1 through 11. However, thread 76 is constructed to have a substantially vertical first face 80 and a substantially undercut second face 82. When implanted, faces 80 and 82 cooperate to engage in interlocking relation with a complementary corresponding female receiving thread. Upon implantation of the device, the resulting undercut thread construction is trapped in the female receiving thread. The construction of FIG. 13 provides the benefits of undercut, while decreasing the cost of producing a thread having an undercut along both faces.

Figure 14:
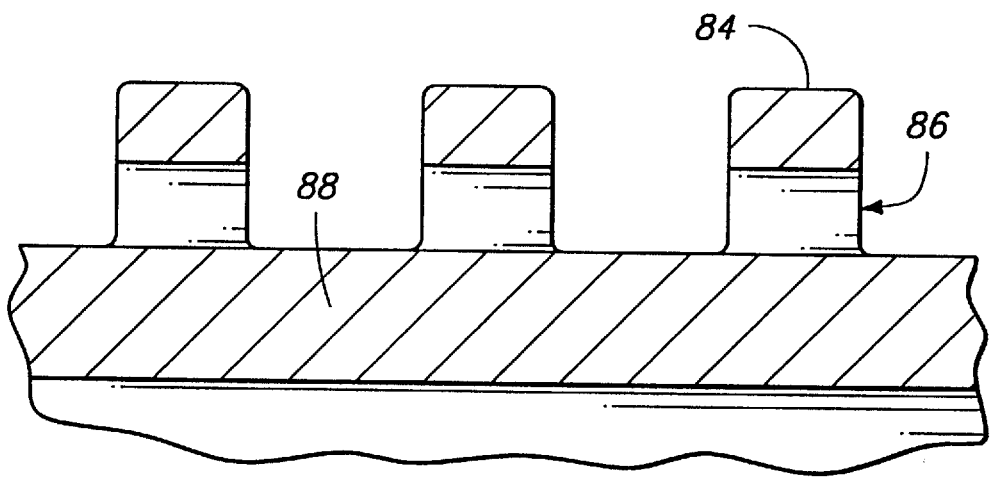
FIG. 14 is a fragmentary and enlarged centerline sectional view depicting a vertebral interbody implant having a third alternative undercut thread construction.

FIG. 14 is yet another alternative construction of a thread 84 having undercut features 86 on an implant 88. Undercut 86 is provided by through holes substantially similar to through hole 60 of implant 10 pursuant to FIGS. 1 through 11. However, the undercut 86 of FIG. 14 is less preferred since immediate fixation is difficult, if not impossible to impart immediately after implantation of implant 88 within a bone bed. One technique for enabling immediate fixation is to also provide bone cement, such as polymethyl methacrylate (PMMA) which is inserted into the prepared bed as well as into holes 86 so that immediate fixation can occur via undercut 86 with the bone bed upon implantation of implant 88 there along. Additionally, or alternatively, undercut 86 can take on the form of a localized, or discreet undercut that extends into a base portion of thread 84 along only a discrete portion(s). Even furthermore, through holes 60 can alternatively extend between a side face of thread 84 and the radial outermost face of the thread. Such a configuration will provide for undercut fixation.

Alternatively, the thread constructions depicted in FIGS. 1–14 can be formed by any of a number of cross-sectional configurations of one or more splines extending from a base body, and having an undercut portion. Further examples would include a spline having a vertical first face and an opposite undercut face. The undercut can have a face that is flat, concave, convex or some combination thereof. Furthermore, the first face can be sloped, essentially the opposite of undercut, thinning the spline in locations away from the base body. However, a corresponding undercut must be provided on the second face, in order to ensure interlocking between the implant and a bone bed instantly upon fixation. Another alternative construction has a pair of threads extending about the implant. With such a dual thread construction, the threads start 180 degrees apart, such that cutting forces produced by self-tapping threads will substantially offset one another. Hence, a self-tapping implant will tend to rotate into a pilot hole in a balanced manner, tending to follow the pilot hole. Furthermore, the balanced forces lead to a compact and stable implant that is more readily implanted in close relation with a solid bone bed. Such a relation enhances osteogenic effect, and allows a surgeon to deliver the implant on a long and thin driver. Hence, a smaller incision can be used to perform the surgery (via laparoscopy and thoroscope), resulting in much less trauma and less recovery time to a patient.

Figure 15:
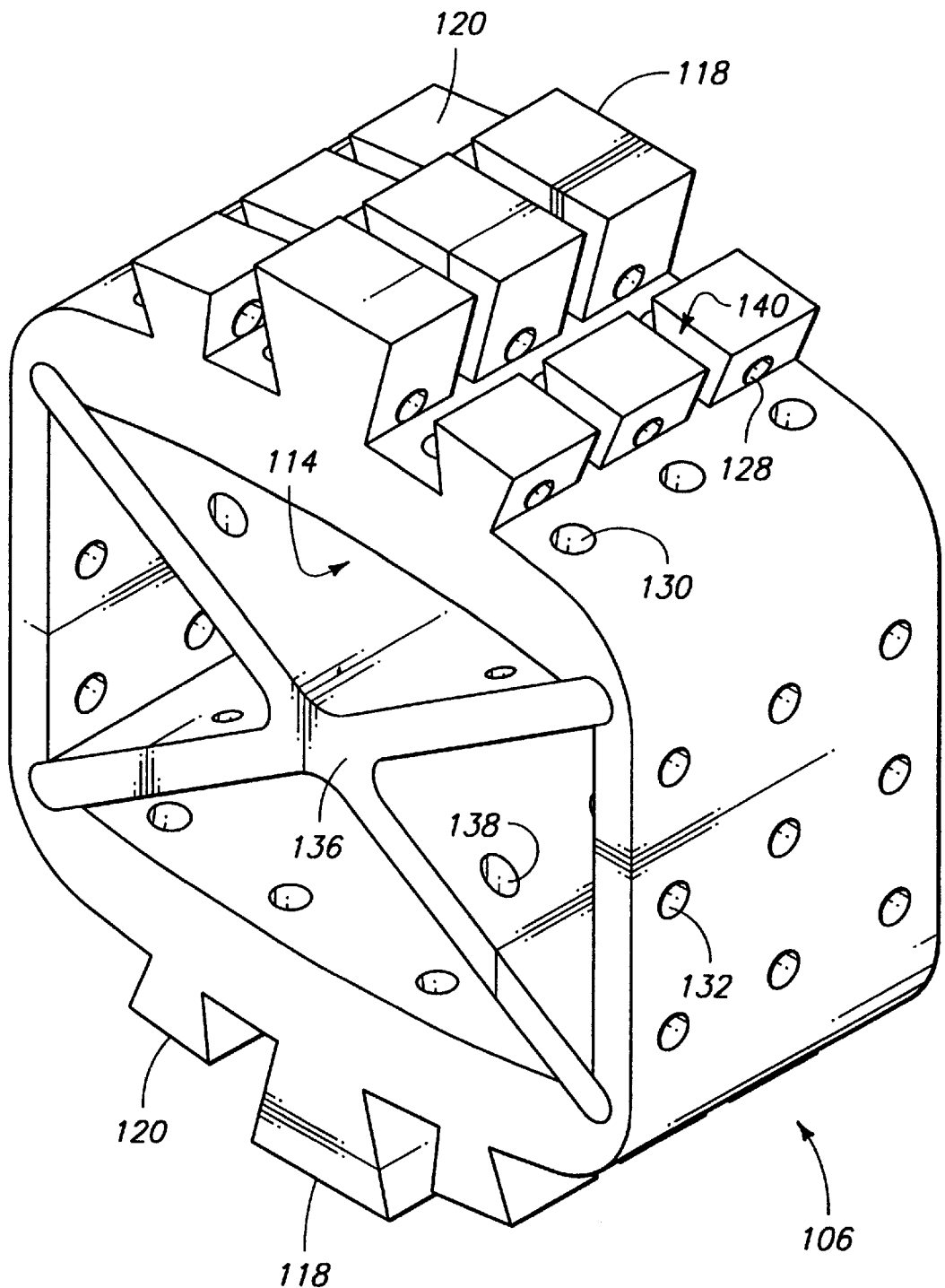
FIG. 15 is a perspective view illustrating a bridging vertebral interbody implant embodying this invention for use in performing a corpectomy.

FIG. 15 illustrates a bone joining implant 106 suitable for use in performing a vertebral corpectomy. A corpectomy involves removal of a vertebral body from the posterior arch of a vertebra. Implant 106 has splines 118 and 120 configured on a top and bottom most outer surface for interlocking in bone beds of vertebrae adjacent to the vertebra to be removed. Implant 106 is first inserted into the bone beds of the vertebrae above and below the corpectomy after they are prepared. This option allows stabilizing the two healthy vertebrae 90 and 94 before removing the vertebral body of vertebra 92. Otherwise, vertebra 92 would be dangerously destabilized. The implant has an open central receiving cavity 114 that envelopes the vertebra to be removed. Following implantation, the vertebra is remove, after which a reinforcing brace, or medial cruciate baffle 136 is mounted within implant 106 to strengthen the structural bridging resulting there between.

Figure 16:
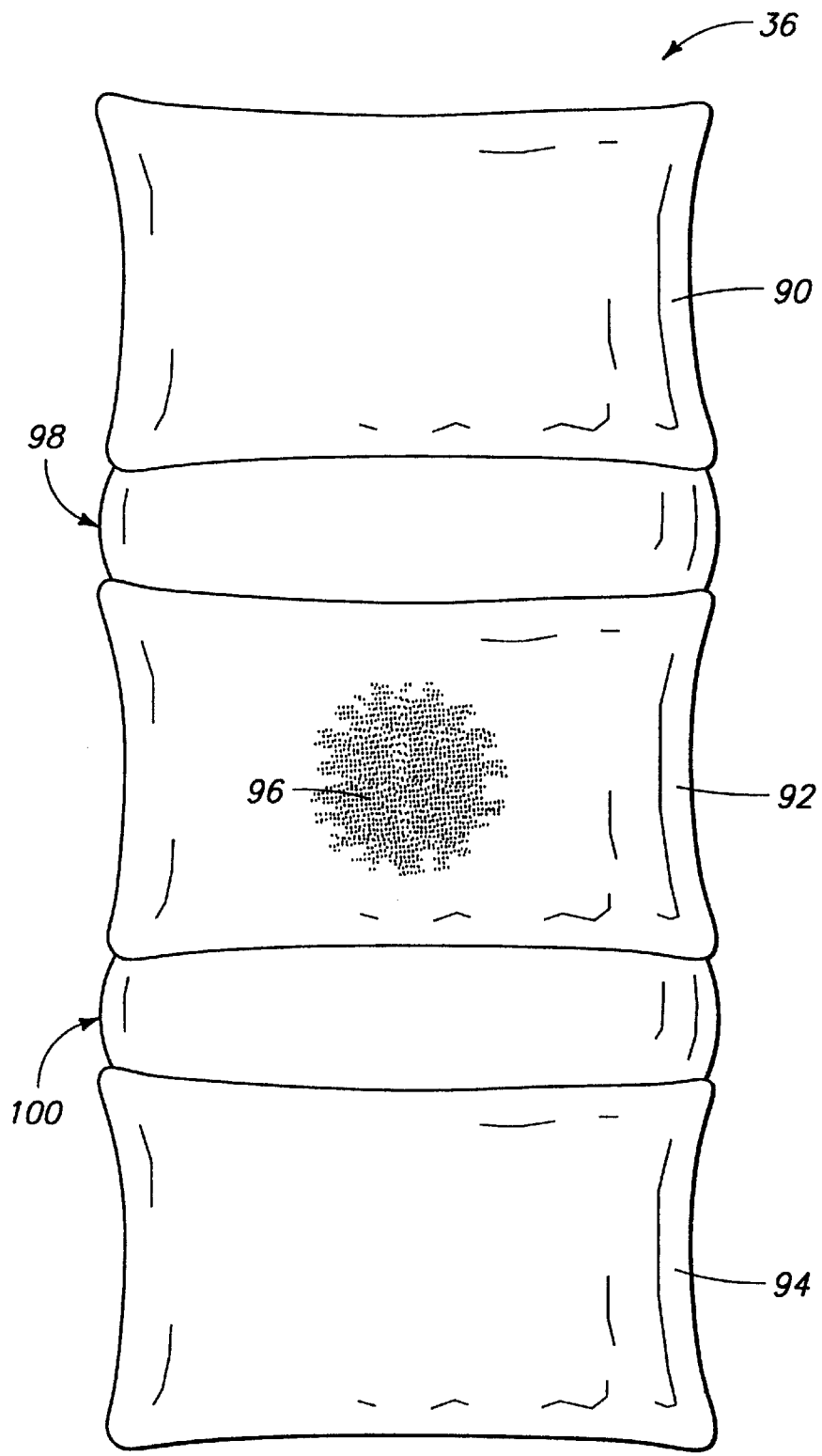
FIG. 16 is a front elevational view of a vertebral structure showing three vertebrae, with a midmost one having a visible cancerous or benign tumor.

FIG. 16 illustrates a portion of vertebral column 36 wherein a middle vertebra 92 has a cancerous tumor 96. Such a condition is a suitable candidate for a corpectomy, which requires complete removal of the vertebral body to extract cancerous tumor 96, and removal of discs 98 and 100. However, it is very difficult to perform such an operation without stabilizing the healthy vertebra first due to the tendency of surrounding muscles and soft tissue to compressively set the spine, driving vertebral bodies 90 and 94 closer together. The main body portion of vertebra 92 is removed, and a posterior portion forming the arch is left intact, thereby removing significant protection to the spinal cord and nerve structures. Therefore, it becomes necessary to maintain the positions of vertebrae 90 and 94 during removal of vertebra 92 until suitable implant material and/or implants can be inserted there between.

Figure 17:
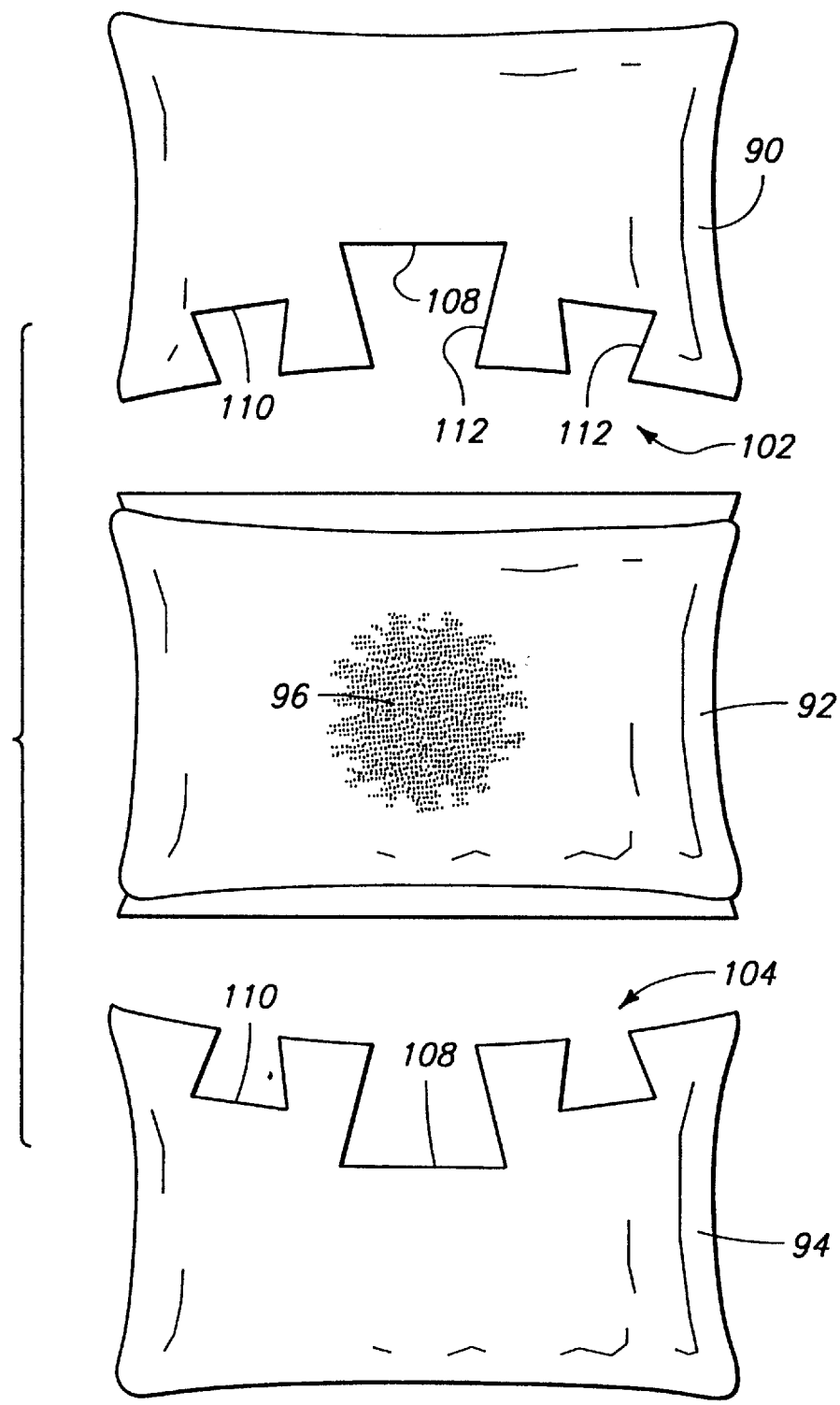
FIG. 17 is a front elevational view of the vertebral structure of FIG. 16 depicting the cephalad and caudad vertebrae prepared to receive the alternatively constructed interbody implant of FIG. 15.

According to FIG. 17, vertebrae 90 and 94 are cut to prepare bone beds 102 and 104 for receiving the bone bridging implant 106 (FIG. 16) of this invention. Each of beds 102 and 104 is formed from a single, centrally located and axially extending undercut groove 108 and a pair of laterally positioned and axially extending smaller grooves 110. Grooves 108 and 110 are preferably cut into vertebrae 90 and 94 with a saw or milling head, forming beds 102 and 104, respectively. Undercuts 112 in each groove ensure interlocking of implant 106 as discussed below. Preferably, beds 102 and 104 are prepared while vertebra 92 is left in position.

Figure 18:
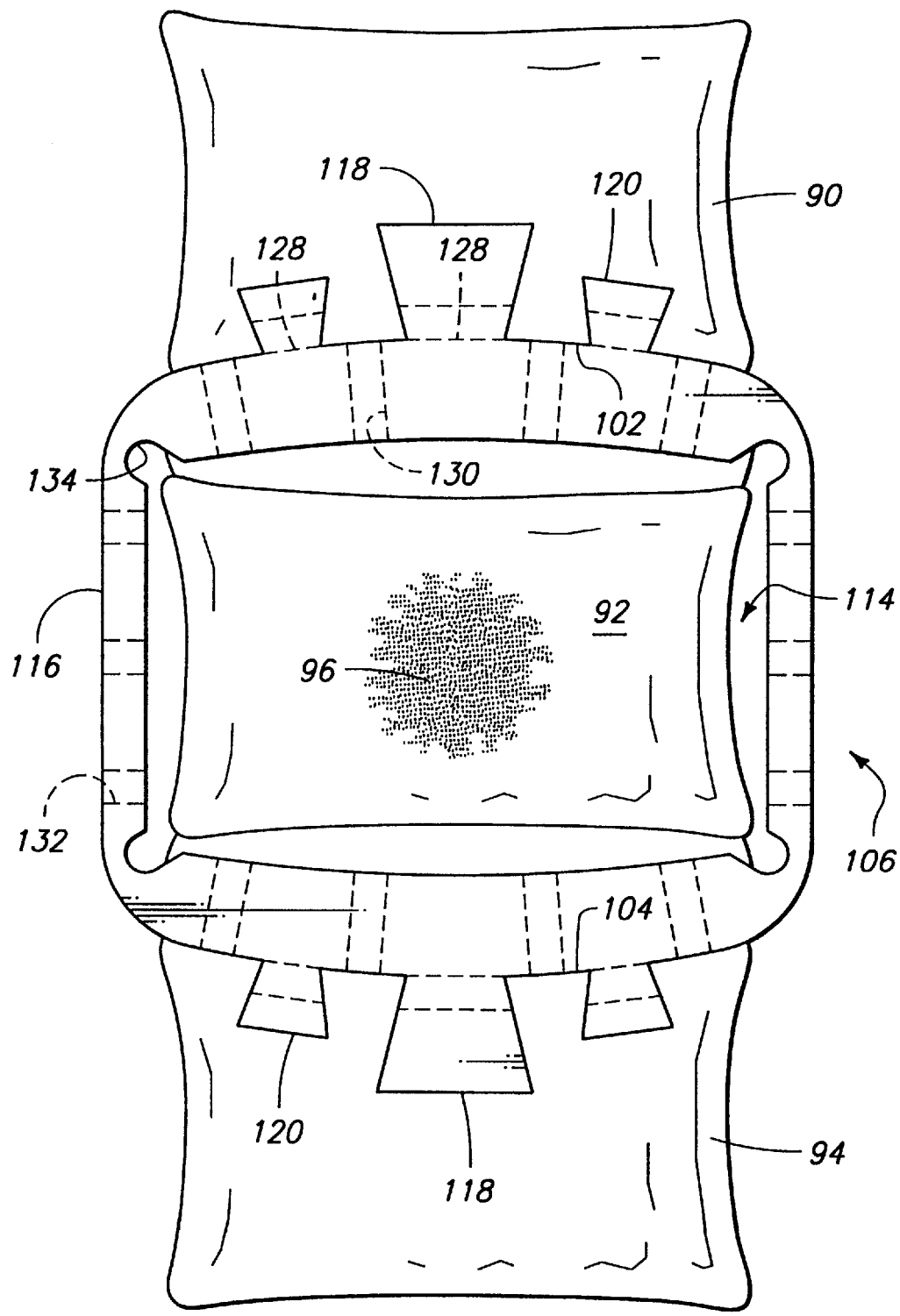
FIG. 18 is a front elevational view of the vertebral structure of FIG. 17 after receiving the alternatively constructed interbody implant.

According to FIG. 18, implant 106 is inserted into interlocking and fixed relation with vertebrae 90 and 92, along beds 102 and 104. Subsequently, vertebra 92, which is contained within the receiving cavity 114 of implant 106 is cut from the arch extending posteriorally there along, and removed from the implant.

Implant 106 of FIG. 18 has a hoop shaped somewhat-rectangular base body 116, defining receiving cavity 114 therein. An elongated and axially extending large spline 118 and neighboring adjacently disposed small splines 120 are configured on a top most 122 and bottom most 124 face of body 116. Splines 118 and 120 both have an undercut 126 constructed and arranged to engage in dove-tailed relation with undercut grooves 108 and 110 respectively. In this manner, implant 106 is mated in immediate fixed relation between vertebrae 90 and 94, forming a structural bridge there between. Subsequently, the vertebral body of vertebra 92 is removed therefrom.

Implant 106 also has horizontally extending through holes 128 formed in each spline 118 and 120. Additionally, vertically extending fenestrations 130, as well as horizontally extending fenestrations 132 are provided in base body 116 for facilitating bony ingrowth and through growth there through. Furthermore, a plurality of brace receiving grooves 134 are provided, one at each corner of cavity 114 for receiving a reinforcing brace (FIGS. 15 and 19) subsequent to removal of vertebra 32 there from.

According to FIG. 19, reinforcing brace 136 is inserted within implant 106 so as to structurally enforce the box-shaped base body configuration. Preferably, brace 136 includes fenestrations 138 for facilitating bony ingrowth and through growth there along. Preferably, bone graft material 20 is also inserted in the remaining portions of cavity 114, along brace 136. The bone graft material further facilitates ingrowth and through growth between vertebra 90 and 94, and with graft material 20. Additionally, a cavity 139 is shown optionally in FIG. 19, in which bone graft material 20 can be packed to facilitate ingrowth and through growth.

FIG. 15 also discloses an interrupted configuration for each of splines 118 and 120. Interruptions 140 prevent inadvertent axial displacement of implant 106 subsequent to implantation. Interruptions 140 in splines 118 and 120 serve to prevent axial motion of each spline within each groove 108 and 110, respectively. Additionally, or alternatively PMMA can also be inserted between the splines and grooves during implantation. The PMMA, or bone cement facilitates fixation between the implant and grooves 108 and 110. PMMA can partially fill through holes 128 and/or fenestrations 130 and 132, further joining with the vertebral bodies 90 and 94 to prevent motion there between.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

I claim:

1. A bone joining implant, comprising:
    a generally cylindrical base body having a leading end and a trailing end;
    a helical thread formed around an outer periphery of the base body and providing a self-tapping portion extending along the leading end of the base body comprising a plurality of thread segments generally increasing in radial height from an advancing end to a trailing end; and
    a hole extending generally axially of the base body through the thread, such hole configured to interrupt the thread along the leading end so as to form at least in part the self-tapping portion.

2. The bone joining implant of claim 1 further comprising a fenestration provided in the base body and configured to interrupt the thread so as to form at least in part the self-tapping portion.

3. The bone joining implant of claim 1 wherein the thread comprises an undercut thread configured to mate in self-tapping, interlocking engagement with each of a pair of bone bodies to be joined.

4. The bone joining implant of claim 1 wherein the self-tapping portion comprises a fenestration within the base body positioned and arrange to interrupt the thread.

5. The bone joining implant of claim 1 wherein the self-tapping portion comprises a hole extending through and generally transverse to the thread between opposed faces and sized so as to interrupt the thread along the leading end.

6. The bone joining implant of claim 1 wherein the self-tapping portion comprises at least one cutout portion provided in the thread and configured to interrupt at least one portion of the thread.

7. The bone joining implant of claim 1 further comprising a hollow portion provided within the base body and a plurality of fenestrations extending between the hollow portion and an outer surface, at least one of the fenestrations configured to interrupt the thread so as to provide such self-tapping portion.

8. A vertebral interbody implant, comprising:
    a base body extending from a leading end to a trailing end;
    a helical self-tapping bone thread comprising at least one thread segment formed around the base body, a tapered portion of the thread extending along the leading end portion; and
    a thread interruption comprising a hole extending through and generally transverse to the thread between opposed faces and sized to interrupt the thread along the leading end.

9. The vertebral interbody implant of claim 8 wherein the tapered portion of the bone thread comprises a thread interruption defining adjacent thread segments that cooperate to impart self-tapping features to the thread.

10. The vertebral interbody implant of claim 9 wherein the thread interruption comprises a fenestration formed within the base body.

11. The vertebral interbody implant of claim 9 wherein the thread interruption comprises a cutout portion provided in the thread and configured to interrupt at least one portion of the thread.

12. The vertebral interbody implant of claim 8 wherein the thread comprises an undercut thread.

13. The vertebral interbody implant of claim 8 wherein the helical self-tapping bone thread comprises a plurality of thread segments extending along the base body, progressive thread segments within the tapered portion extending from the leading end toward the trailing end being sized progressively larger in radial dimension so as to impart self-tapping features along each thread interruption.

14. The vertebral interbody implant of claim 8 wherein the tapered portion of the thread is discontinuous, comprising interruptions there along.

15. A bone joining member, comprising:
    a generally cylindrical base body extending from a leading end to a trailing end;
    a self-tapping bone thread comprising at least one helical thread segment formed around the base body and a tapered leading end portion having a series of interruptions; and
    a hole extending substantially transversely through the thread and configured to interrupt the thread along the leading end to form a self-tapping portion.

16. The bone joining member of claim 15 wherein the base body further comprises a hollow portion provided within the base body.

17. The bone joining member of claim 16 further comprising a plurality of fenestrations extending from the hollow portion to a radial outer surface, at least one of the fenestrations configured to interrupt the tapered leading end portion of the bone thread.

18. The bone joining member of claim 15 wherein the tapered leading end portion of the thread is discontinuous, comprising thread interruptions formed by the hole extending there along.

19. The bone joining member of claim 15 wherein the thread is tapered in height from an advancing end to a trailing end of the tapered leading end portion, the hole provided in the thread along the tapered leading end portion, such hole enabling self-tapping of the implant.

20. The bone joining member of claim 15 further comprising holes extending through the thread along the tapered leading end portion, such holes providing interruptions within the thread along the tapered leading end portion, such interruptions providing at least in part such self-tapping bone thread.

21. The bone joining member of claim 15 wherein the thread comprises an undercut portion configured to engage in interlocking relation with a bone bed of a bone body to be joined.

22. An implant for use in spinal stabilization for placement into a disc space between two vertebrae having end plates of cortical bone and a vertebra interior of cancellous bone, the implant comprising:
    a rigid body having an outer surface with at least one bone bed engaging portion configured to engage a pair of vertebrae to be joined; and
    a self-tapping bone thread comprising at least one helical undercut thread segment formed around the rigid body and a tapered leading end portion having a series of interruptions.

23. The implant of claim 22 wherein the tapered leading end comprises a hole extending generally transversely of the thread cooperating to form a thread interruption operative to impart self-tapping features to the thread.

* * * * *

UNITED STATES PATENT AND TRADEMARK OFFICE
CERTIFICATE OF CORRECTION

PATENT NO.    : 5,885,287

DATED         : March 23, 1999

INVENTOR(S)   : George Bagby

It is certified that error appears in the above-identified patent and that said Letters Patent is hereby corrected as shown below:

Col. 2, line 19, delete "bone bank", and insert --bone banks--.

Col. 2, line 55, delete "responsive", and insert --response--.

Col. 3, line 28, delete "in growth", and insert --ingrowth--.

Col. 4, line 54, delete "in-growth", and insert --ingrowth--.

Col. 5, line 47, delete "BONE BODIES", and insert --bone bodies--.

Col. 6, line 15, delete "pair of implants 10 are", and insert --pair of implants 10 is--.

Col. 9, line 2, delete "(i.e. No other", and insert --(i.e., no other--.

Col. 9, line 9, delete "thread 14 are", and insert --thread 14 is--.

Col. 10, line 21, delete "threading in into", and insert --threading it into--.

UNITED STATES PATENT AND TRADEMARK OFFICE
CERTIFICATE OF CORRECTION

PATENT NO. : 5,885,287

DATED : March 23, 1999

INVENTOR(S) : George Bagby

It is certified that error appears in the above-identified patent and that said Letters Patent is hereby corrected as shown below:

Col. 10, line 33, delete "inter-locking", and insert --interlocking--.

Col. 10, line 63, delete "fenestrations 24 enjoins", and insert --fenestrations 24 enjoin--.

Col. 12, line 34, delete "fenestrations 22 allows", and insert --fenestrations 22 allow--.

Col. 13, line 17, delete "or discreet undercut", and insert --or discrete undercut--.

Col. 13, line 60, delete "vertebra is remove,", and insert --vertebra is removed,--.

Col. 14, line 29, delete "extending posteriorally", and insert --extending posteriorly--.

UNITED STATES PATENT AND TRADEMARK OFFICE
CERTIFICATE OF CORRECTION

PATENT NO. : 5,885,287

DATED : March 23, 1999

INVENTOR(S) : George Bagby

It is certified that error appears in the above-identified patent and that said Letters Patent is hereby corrected as shown below:

Col. 14, line 47, delete "134 are provided", and insert --134 is provided--.

Col. 14, line 49, delete "vertebra 32 there from", and insert --vertebra 32 therefrom--.

Col. 14, line 57, delete "between vertebra 90 and 94", and insert --between vertebrae 90 and 94--.

In the Claims:

Col. 15, line 37, Claim 4, delete "and arrange", and insert --and arranged--.

Signed and Sealed this

Thirty-first Day of August, 1999

Attest:

Q. TODD DICKINSON

*Attesting Officer*     Acting Commissioner of Patents and Trademarks